United States Patent
Hunkapiller et al.

(10) Patent No.: US 6,232,067 B1
(45) Date of Patent: May 15, 2001

(54) ADAPTER DIRECTED EXPRESSION ANALYSIS

(75) Inventors: Michael W. Hunkapiller, San Carlos; John H. Richards, Bradbury, both of CA (US)

(73) Assignee: The Perkin-Elmer Corporation, Foster City, CA (US)

( * ) Notice: Subject to any disclaimer, the term of this patent is extended or adjusted under 35 U.S.C. 154(b) by 0 days.

(21) Appl. No.: 09/135,381

(22) Filed: Aug. 17, 1998

(51) Int. Cl.$^7$ ........................................................ C12Q 1/68
(52) U.S. Cl. ..................... 435/6; 435/5; 435/7; 435/91.1; 435/91.2; 436/501; 536/26; 536/27; 536/28; 536/77; 536/78
(58) Field of Search ................................. 435/6, 5, 7, 91, 435/91.1, 91.2; 436/501; 536/26, 27, 28; 935/77, 78

(56) References Cited

U.S. PATENT DOCUMENTS

| | | | |
|---|---|---|---|
| 4,731,325 | * | 3/1988 | Palva et al. ............................... 435/6 |
| 5,242,794 | | 9/1993 | Hunkapiller . |
| 5,631,134 | * | 5/1997 | Cantor ....................................... 435/6 |
| 5,710,000 | | 1/1998 | Gingeras et al. . |
| 5,800,994 | * | 9/1998 | Martinelli et al. ........................ 435/6 |
| 5,858,751 | * | 1/1999 | Paulson et al. ....................... 435/193 |

FOREIGN PATENT DOCUMENTS

| | | |
|---|---|---|
| 0735144 | 10/1996 | (EP) . |
| WO94/01582 | 1/1994 | (WO) . |
| WO95/04160 | 2/1995 | (WO) . |
| WO96/41011 | 12/1996 | (WO) . |
| WO97/27317 | 7/1997 | (WO) . |
| WO97/31256 | 8/1997 | (WO) . |

OTHER PUBLICATIONS

Unrau et al., "Non–Cloning Amplification of Specific DNA Fragments From Whole Genomic DNA Digest Using DNA Indexers," *Gene* NL, Elsevier Biomedical Press, Amersdam 145:163–169.

* cited by examiner

*Primary Examiner*—W. Gary Jones
*Assistant Examiner*—Janell E. Taylor
(74) *Attorney, Agent, or Firm*—Scott R. Bortner

(57) ABSTRACT

The present invention relate to methods and compositions for simultaneously analyzing multiple different polynucleotides of a polynucleotide composition comprising multiple diverse polynucleotide sequences. The subject methods and compositions may also be applied to analyze or identify single polynucleotides; however, the subject methods and compositions are particularly useful for analyzing large diverse populations of polynucleotides, e.g., cDNA libraries. Most embodiments of the invention involve hybridizing terminus probes (of known base sequence) and internal fragment probes (of known base sequence) at adjacent positions on an adapter-modified restriction fragment generated from polynucleotide for analysis, and subsequently joining the terminus probes and internal fragment probes to each other. The terminus probe hybridizes to bases of restriction endonuclease recognition site present at the terminus of a restriction fragment generated from the polynucleotide for analysis. Internal fragment probes hybridizes to the same strand of the restriction fragment that the terminus probe hybridizes to and hybridizes to the restriction fragment portion of adapter-modified representative restriction fragments. The terminus probes and internal fragment probes may be marked so as to facilitate the simultaneous testing of multiple polynucleotides for the presence of many possible nucleotide base sequences. The identity or expression of a particular polynucleotide of interest may be ascertained (or at least partially determined) by producing a short identifier sequence derived from the nucleotide base sequence information obtained from (1) the hybridization of a terminus probe and an internal fragment probe, each of known base sequence, at adjacent positions on a polynucleotide of interest, and (2) the recognition site of a restriction endonuclease used to generate the polynucleotide molecule of interest. Multiple identification sequences may be obtained in parallel, thereby permitting the rapid characterization of a large number of diverse polynucleotides. Parallel processing may be achieved by differentially marking terminus probes or internal fragment probes. Parallel processing may be achieved by using ordered arrays of oligonucleotides that are terminus probes.

35 Claims, 6 Drawing Sheets

ADAPTER DIRECTED EXPRESSION ANALYSIS

FIELD OF THE INVENTION

Embodiment sof the invnetion are in the field of polynucleotide analysis throught the use of multiple hydrization probes.

BACKGROUND

The cells that constitute different tissues in an organism, although having the same genomic DNA, differ significantly from one another with respect to the specific genes that are expressed and the levels of expression. Similar differences in gene expression can be observed when comparing cells that are obtained from a healthy organism and corresponding cells from an organism manifesting a disease state. Other examples of variations in gene expression include changes induced by exposing a cell to a pharmaceutical compound or toxin. It is of interest to provide methods for analyzing changes in gene expression. Methods of analyzing gene expression find wide use in both research and diagnostics.

SUMMARY

Embodiments of the invention described herein relate to methods of analyzing an individual polynucleotide or a polynucleotide mixture comprising multiple diverse polynucleotides, typically a cDNA mixture formed from an RNA population of interest. Not only is the analysis of RNA populations of major interest in research, such analysis may be used to predict, diagnose, or treat a variety of diseases. Various embodiments of the invention permit the simultaneous analysis of a large number of different mRNA molecules that form a given mRNA population. Various embodiments of the invention also permit the convenient isolation of polynucleotides of interest identified through the subject analytical techniques.

In accordance with the description of the invention provided herein, the identity of a particular polynucleotide of interest may be ascertained by producing a short identifier sequence based on the nucleotide sequence information obtained from (1) the recognition site of a restriction endonuclease used to generate a restriction fragment from the polynucleotide of interest, and (2) the hybridization of: (i) a terminus probe of known sequence, and (ii) an internal fragment probe of known sequence, at adjacent positions on the polynucleotide of interest. Polynucleotide sequence databases may be conveniently searched for previously identified polynucleotide sequences that match or partially match the identifier sequence. Alternatively, the subject methods may be used to "fingerprint" complex polynucleotide populations without the need to generate identifier sequences. The identification sequences may also be used to develop oligonucleotide primers (or probes) to isolate the polynucleotides from which the identifier sequence is derived.

In preferred embodiments of the invention, representative restriction fragments for analysis are joined to adapters prior to contacting either terminus probes or internal fragments probes. Multiple identifier sequences may be obtained in parallel, thereby permitting the rapid characterization of a large number of polynucleotides. The terminus probe and internal fragment probe as used in the subject methods may each be identified by a "marker" that is correlated with the known base sequence of the probe oligonucleotide so as to facilitate the rapid characterization of a large number of diverse polynucleotides in parallel. Parallel analysis of multiple diverse polynucleotides may be carried by using ordered arrays of oligonucleotides (terminus probes) such that the position of the oligonucleotides in the array serve as markers to identify the base sequence of the oligonucleotide in the array.

In one embodiment of the invention, methods are provided for analyzing diverse polynucleotide mixtures such as a cDNA mixture generated from an RNA population. Restriction fragments are formed by digesting the polynucleotide population for analysis with a restriction endonuclease. Preferably, representative restriction fragments are generated from the different cDNA molecules in the mixture in such a way that only a single restriction fragment is recovered for each polynucleotide analyzed. By employing representative restriction fragments, quantitative (or semi-quantitative) measurements of the relative amounts of different polynucleotides in a polynucleotide mixture for analysis may be greatly facilitated. Adapters may be ligated to the termini of the representative restriction fragments so as to produce a set of adapter-modified representative restriction fragments. The representative restriction fragments may then be optionally amplified in a nucleic acid amplification reaction employing primers specific for the adapters, thereby producing an amplified set of adapter-modified representative restriction fragments. The amplified set of adapter-modified representative restriction fragments (or a corresponding non-amplified set) may then be contacted under nucleic acid hybridization conditions with marked terminus probes so that hybridization may take place between each of the different adapter-modified representative restriction fragments and each terminus probe present so as to permit hybridization of the probe to complementary strands of the matching adapter-modified representative restriction fragments. Terminus probes may be marked by virtue of their location on an oligonucleotide array. An oligonucleotide array comprising a plurality of oligonucleotide features, wherein each feature of the array is a terminus probe, may be used to analyze a plurality of polynucleotides in parallel. After hybridization with the terminus probe, the adapter-modified representative restriction fragments that have hybridized to the array are contacted (under nucleic acid hybridization conditions) with a labeled probe solution comprising at least one internal fragment probe. The internal fragment probes may be marked, preferably with a fluorescent dye, so as to identify array sites at which hybridization has occurred. Solutions containing multiple differentially labeled internal fragment probes may be used to simultaneously test different internal fragment probes for hybridization to multiple different representative restriction fragments in parallel. Labeled probes that have hybridized to adapter-modified representative restriction fragments at positions adjacent to the terminus of the array feature oligonucleotides are subsequently joined (e.g., by ligase catalyzed ligation), thereby covalently attaching the internal fragment probe to the array. The location of the joined terminus probe or probes on the array may subsequently be identified, thus serving to identify which of the oligonucleotide features (terminus probes) are complementary to a given representative restriction fragment. Sequence information from the internal fragment probe and the terminus probe ligated to the internal fragment probe may be used to obtain an identifier sequence corresponding to the restriction fragment that hybridized to the array at a given feature. Alternatively, arrays of terminus probes may be used to "fingerprint" complex polynucleotide populations with or without the generation of identifier sequences.

Other embodiments of the invention include oligonucleotide arrays comprising features that are complete sets of terminus probes. Embodiments of the subject arrays include arrays that comprise multiple subarrays, wherein at least two of the subarrays comprise the same set of terminus probes; preferably each set of terminus probes in each subarray is a complete set of terminus probes. Each subarray may be organized so as to provide for the addition of oligonucleotide probe solution to one array subunits without having the solution contacting the other subunits.

In another embodiment of the invention, terminus probes and internal fragment probes are hybridized at adjacent positions on an adapter-modified representative restriction fragment (or adapter-modified restriction fragments) and subsequently joined to each other prior to the step of immobilization on a sorting array. The use of sorting arrays permits the step of joining terminus probes and internal fragment probes to take place in solution rather than on an array. In embodiments of the invention employing sorting arrays, either the terminus probes or the internal fragment probes may be marked with an array sorting signal. In embodiments of the invention employing a sorting array, sorting signal marked terminus, probes are used in conjunction with the internal fragment probes that are marked with a detectable label. Conversely, internal fragment probes may be marked with sorting signals when used in conjunction with detectably labeled terminus probes. For example, a representative restriction fragment is formed from a polynucleotide of interest. Adaptors are subsequently joined to the termini of the representative restriction fragment so as to produce adapter-modified representative restriction fragments. Preferably, the adapter-modified representative restriction fragments are amplified in a nucleic acid amplification reaction (e.g., PCR) with primers that specifically hybridize to the two adapters so as to increase sensitivity. A terminus probe is then hybridized to a strand of the adapter-modified representative restriction fragment. An internal fragment probe of known sequence is then hybridized to the same strand of the adapter-modified representative restriction fragment at a position adjacent to an end of a terminus probe that has hybridized to the restriction fragment. The internal fragment probes and the terminus probes that have hybridized at adjacent positions on a strand of an adapter-modified restriction fragment are then joined together, e.g., ligated, while hybridized to the strand of the adapter-modified representative restriction fragment. The array sorting signals on the probes may be used to identify which probe has hybridized to a given adapter-modified restriction fragment by virtue of the ability of the array sorting signal to specifically bind to a receptor for the sorting signal at a predetermined location on an array. The detectable label on the detectable label marked probe joined to an array sorting signal marked probe may be used to identify the sequence of the detectable label marked probe.

Other embodiments of the invention include kits for carrying out the methods of the invention. The kits comprise two or more reagents necessary for carrying out an embodiment of the subject methods. Embodiments of the kits of the invention may include an oligonucleotide array and a set of internal fragment probes and/or terminus probes designed for use in conjunction with the arrays in the kit. The kits may further comprise adapters designed to be used in conjunction with the subject arrays and labeled oligonucleotide probe sets. The inventions also include kits for carrying out embodiments of the invention employing probes that are marked with sorting signals. Kits for use with sorting signals comprise a sorting signal array and probes marked with sorting signals for use in conjunction with the arrays. Optionally, the kits of the invention may comprise other reagents required for performing the subject methods, such reagents include, primers, buffers, DNA, polymerases, DNA ligases, and restriction endonucleases.

DEFINITIONS

Figure 1A:
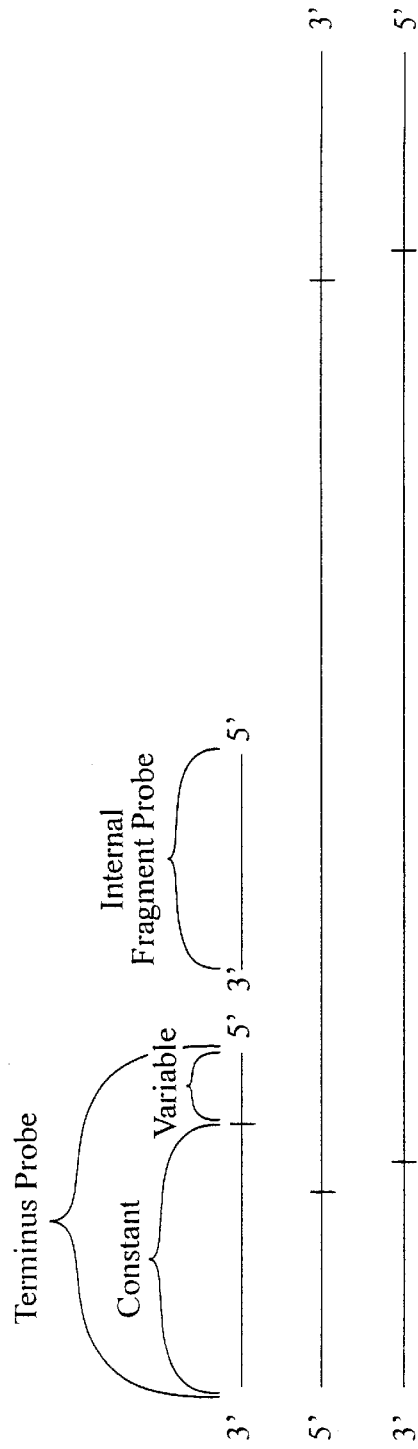
FIGS. 1A and 1B are schematic diagrams showing how terminus probes and internal fragment probes may hybridize adapter-modified representative restriction fragments. The variable and constant regions of the terminus probes are indicated. Embodiments of both possible rrealtive orientations of the variable and constant regions on a terminus probe are shown. The vertical lines on the adapter-modiied restriction fragments show the actual junctions between the adapters and the restriction fragment.

1. The term "terminus probe" as used herein refers to an oligonucleotide that is complementary to a specific portion of a strand of an adapter-modified restriction fragment (including restriction fragments that are representative restriction fragments). Terminus probes serve to identify (through hybridization) one or more nucleotides of a restriction fragment that are adjacent to the junction formed between an adapter and a restriction fragment. Terminus probes are complementary to one or more bases adjacent to both sides of the junction. Terminus probes are complementary to bases at and near the junction formed between an adapter and a restriction fragment. Terminus probes may thus be conveniently referred to as complementary to junctions between the adapter and the restriction fragment, even though the actual junction is formed by the juxtaposition of only two bases. Because adapter-modified restriction fragments may have two junctions between adapters and the restriction fragment (one for each terminus of the restriction fragment), the terminus probe may be selected so as to be complementary nucleotide bases at either of the two junctions (but not both junctions). In many embodiments of the invention, multiple terminus probes are selected to be used in conjunction with one another, i.e., sets of terminus probes, thereby providing for the simultaneous analysis of multiple polynucleotides when the different probes are used in conjunction with one another. The different terminus probes that form a given set of terminus probes are selected so as to hybridize to the equivalent junction and some strands of the different adapter-modified restriction fragments produced in a given embodiment of the subject methods. By "equivalent junction," it is intended that the junction formed between the same adapter and the same restriction fragment terminus be used for all the adapter-modified restriction fragment analyzed by a given set of terminus probes.

Terminus probes are said have a "constant region" and a "variable region." A given nucleotide base in a terminus probe is either in the constant region or the variable region, but not both. The "constant region" is said to be constant because the constant regions of a set of terminus probes are functionally the same as each other with respect to their hybridization specificity as used in the methods of the invention. The constant region is complementary to (1) nucleotides of the restriction endonuclease recognition site used to generate a terminus of the restriction fragment for analysis, and (2) at least a portion (and preferably all) of the adapter adjacent to the restriction endonuclease recognition site at the adapter/restriction fragment junction. The length of the constant region will be, in part, determined by (1) the length of the recognition sequence of the relevant restriction endonuclease, and (2) the length of the adapter used in conjunction with restriction fragments. Typically, the length of the constant region is 5–20 nucleotide bases in length. The constant region may extend past the region of the terminus probe designed to hybridize to adapter-modified restriction fragments. This additional probe region may be used to reduce steric hindrance between solid supports and restriction fragment hybridization. The "variable region" is said to be variable because the variable region of a set of terminus probes have different nucleotide base sequences. The variable region of a terminus probe is complementary to a portion (typically 1–8 nucleotide bases) of the restriction fragment that are adjacent to the restriction endonuclease recognition site base or bases at the terminus of the restriction fragment used to form the adapter-modified restriction fragment.

Figure 1B:
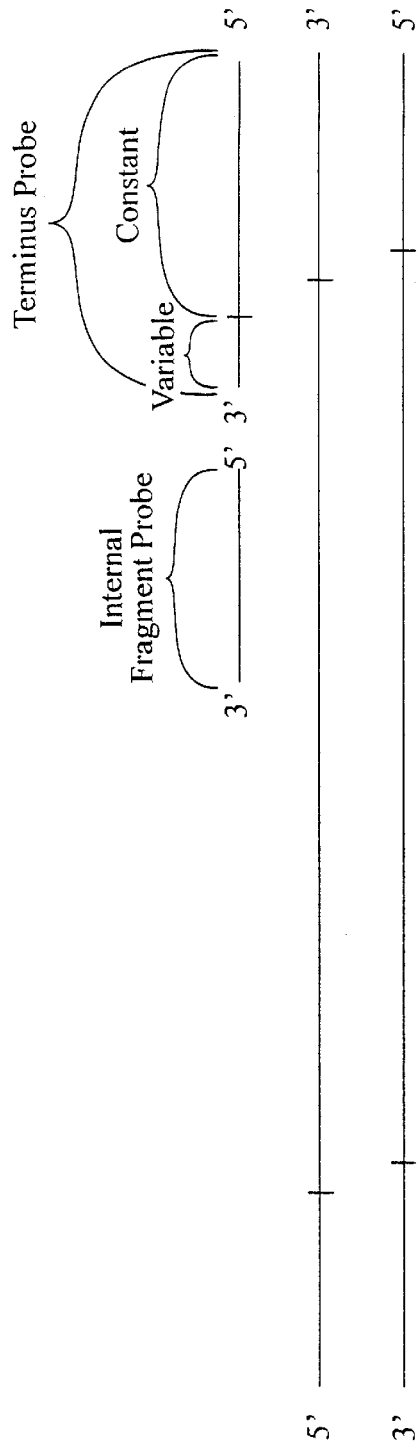
Figure 2:
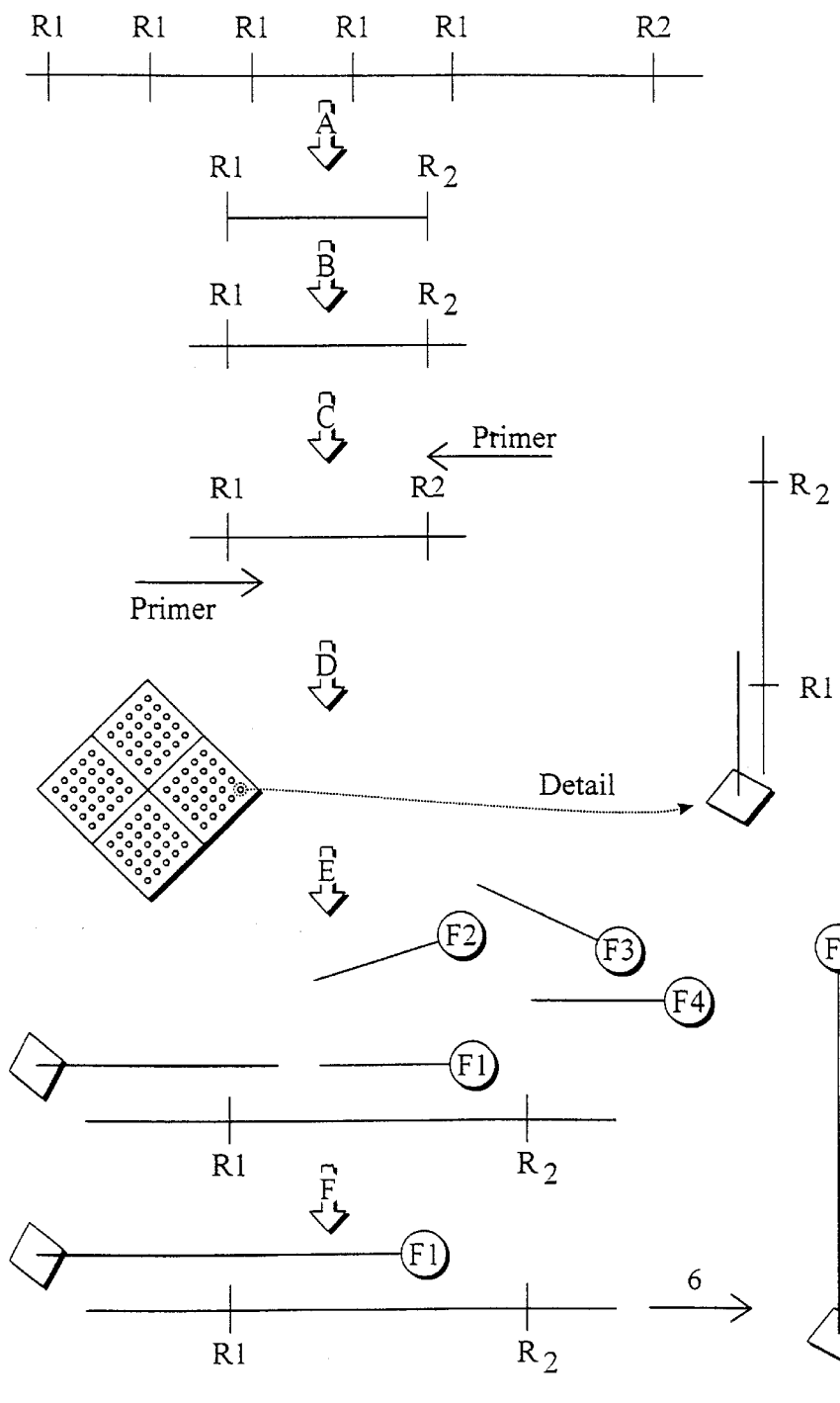
FIG. 2 is a schematic representation of a method of analyzing complex polynucleotides in accordance with the methods of the invention. R1 and R2 are used to indicate restriction sites. Step A indicates the generation of representative restriction fragments from cDNAs. Step B shows the addition of adapters to the representative restriction fragments to form adapter-modified representative restriction fragments. Step C shows the addition of amplification primers and performance of a PCR reaction to generate adapter-modified representative amplification products. Step D shows the hybridization of a strand of an adapter-modified representative restriction fragment to a terminus probes of an array. An overview of an array comprising subarrays is shown. The hybridization of the adapter-modified representative restriction fragment is shown as a detailed view of an individual array feature. Step E shows the hybridization of a fluorescently labeled internal fragment probe to an adapter-modified representative restriction fragment strand hybridized to a terminus probe. The different circled "F"s are used to indicate fluorescent dyes on different internal fragment probes. Only the F1 labeked probe is hybridized. Step F shows the ligation of the terminus probe to internal fragment probe. The adapter-modified representative restriction fragment is washed away in step G.
Figure 3:
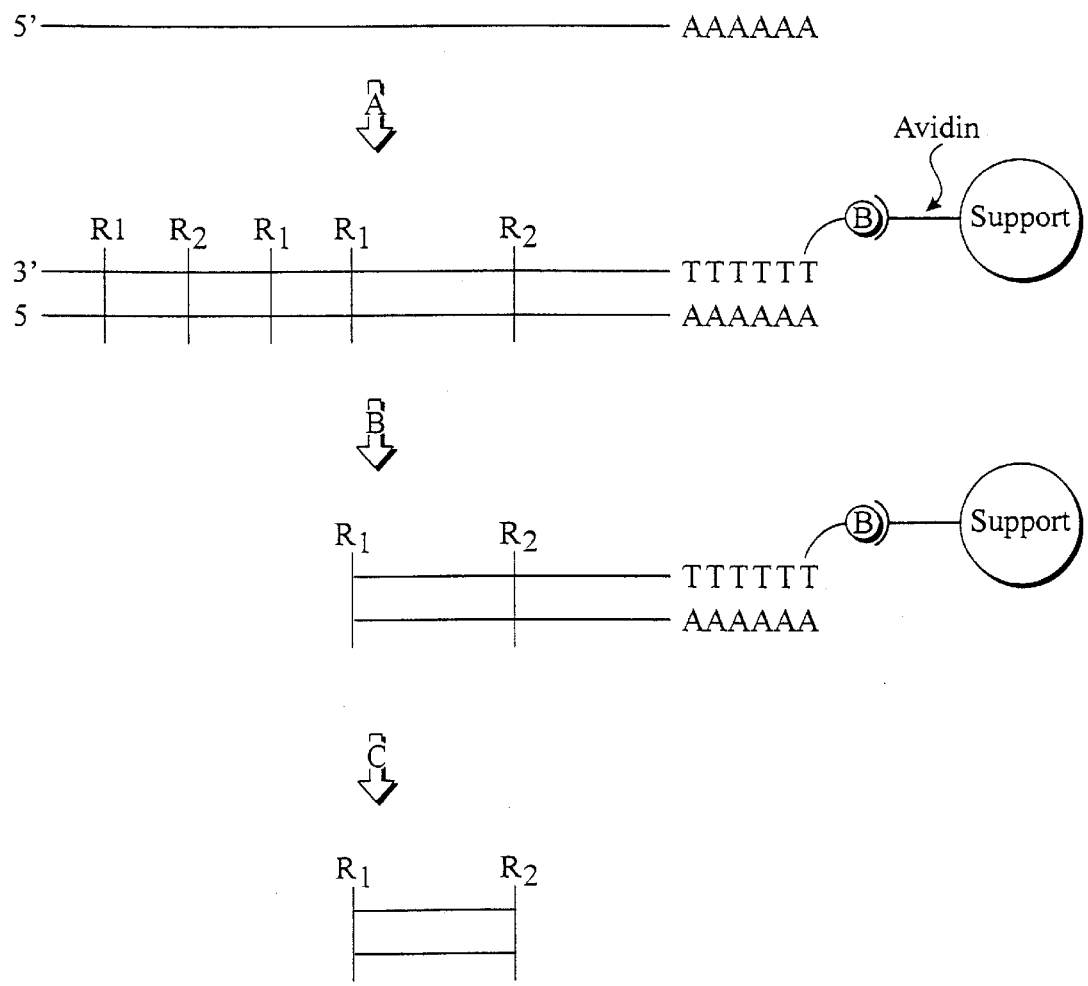
FIG. 3 is a schematic diagram of formation of a representative restriction fragment by sequential restriction endonuclease digestion. In Step A, cDNA from mRNA is formed using a biotinylated poly dT primer and is bound to avidin immobilized on a solid support. The circled B indicates biotin. In Step B, a first restriction endonuclease (R1) is added and the digestion products are removed by washing. In Step C, a second restriction endonuclease R2 is added and the representative restriction fragment is rcovered.
Figure 4:
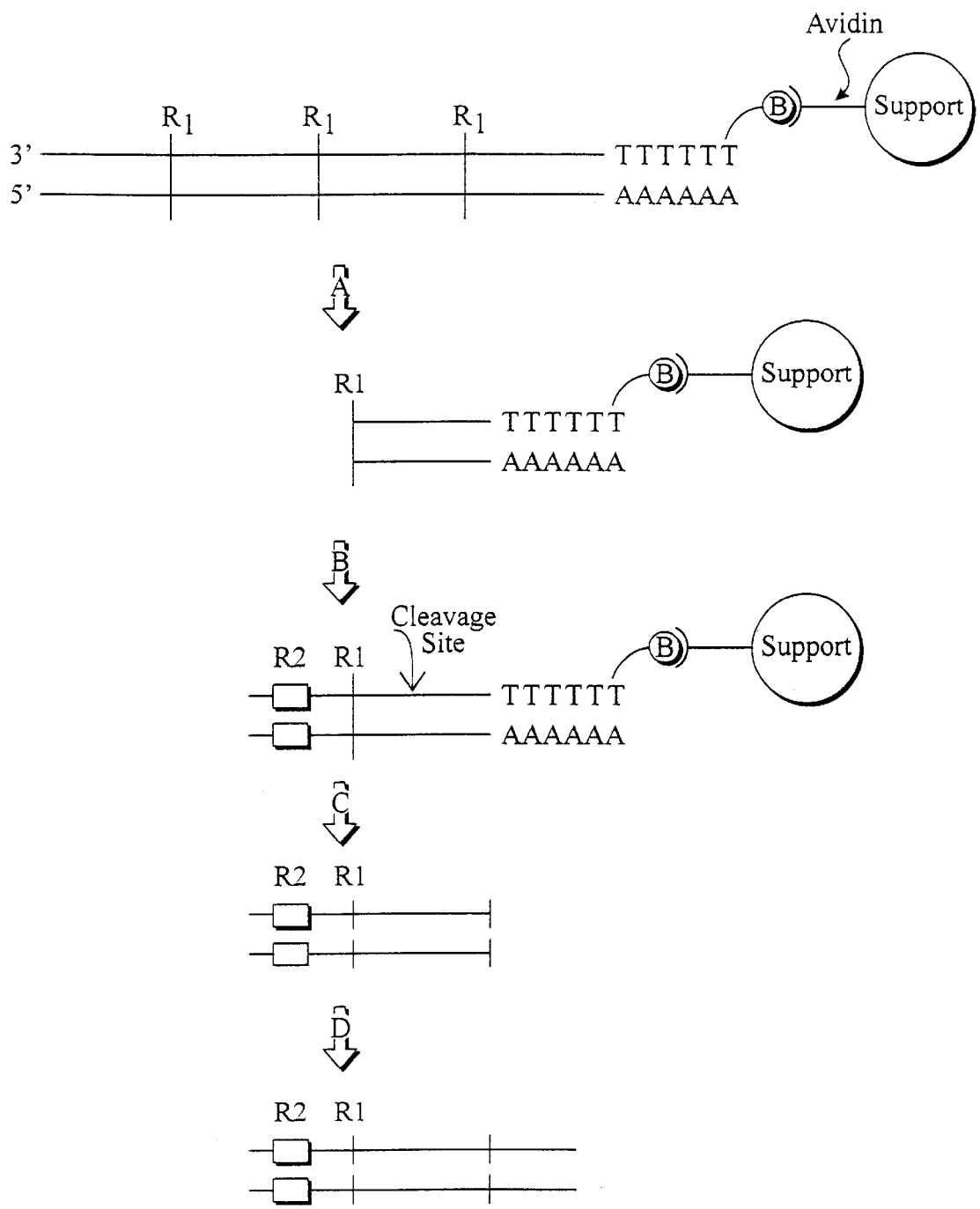
FIG. 4 is a schematic diagram of an embodiment of a technique for generating representative restriction fragments by sequential restriction endonuclease digestion employing a type IIs restriction endonuclease. In Step A, cDNA formed by priming first strand synthesis with a biotinylated poly dT that is bound to avidin immobilized on a solid support is treated with a first restriction endonuclease (R1). In Step B, an adapter having a recognition site (indicated by the bolded rectangle region) for a type IIs restriction endonuclease (R2). In Step C, the type IIs restriction endonuclease is added and the representative restriction fragment isolated. In Step D, a second adapter is added.
Figure 5:
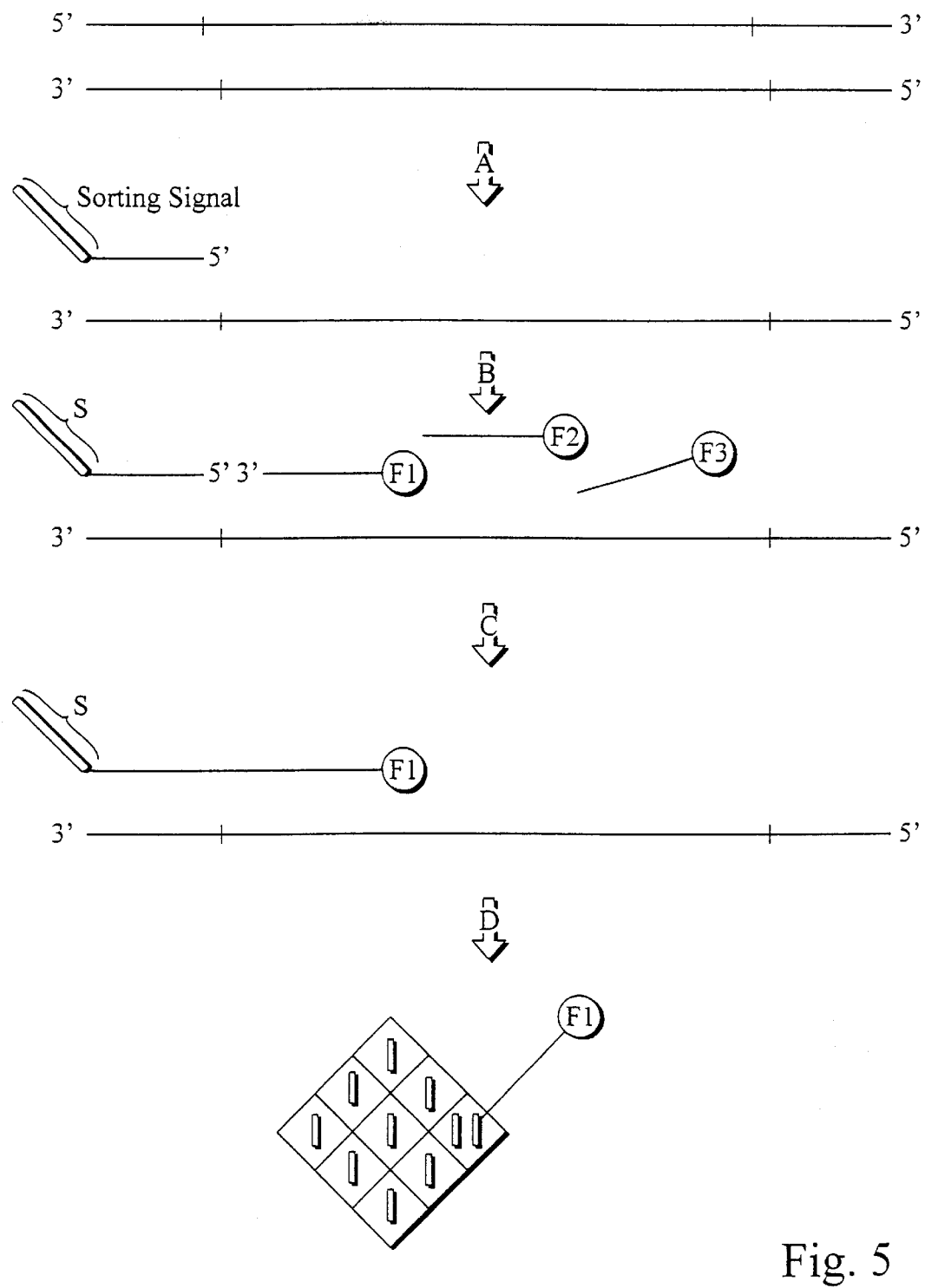
FIG. 5 is a schematic diagram of an embodiment of the invention employing sorting arrays. In Step A, a terminus probe is marked with an array sorting signal (indicated by the rectangle on the 3' end of the probe) is hybridized to a strand of the adapter-modified representative restriction fragment. In Step B, an internal fragment probe is labeled with a fluorescent dye (indicated by a circled "F1") is hybridized at a position adjacent to the hybridized terminus probe. The non-hybridizing internal fragment probes are indicated by the other circled Fs. In Step C, the terminus probe and the internal fragment probe are ligated together. In Step D, the ligated fluorescently labeled probes are contacted with a sorting array and bind to an array sorting signal receptor at the indicated location on a cirting array. The single rectangles on the array indicate un bound array sorting signal receptors.
Figure 6:
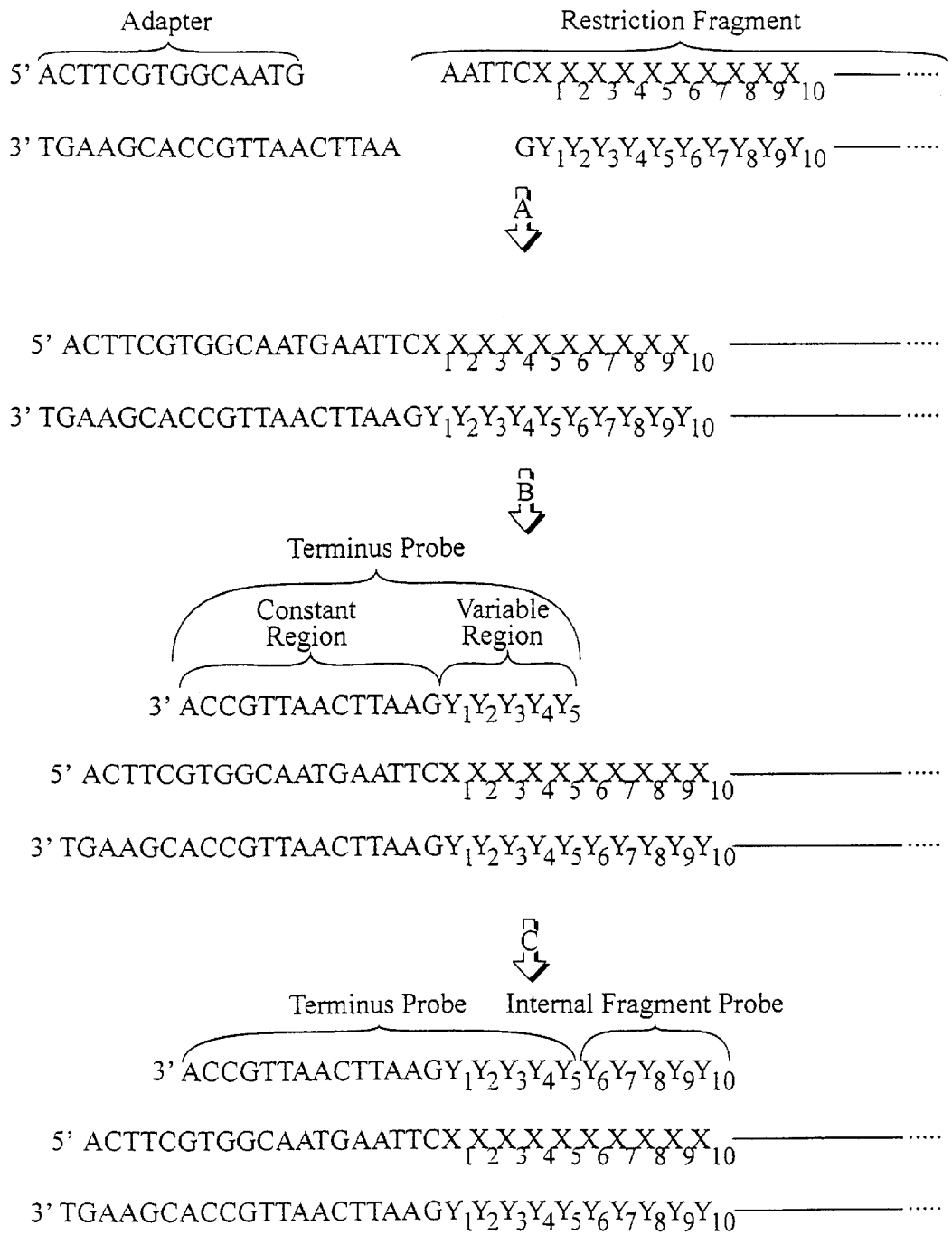
FIG. 6 is a schematic example showing of the joining of an adaptor (for EcoRI) to an end of a representative restriction fragment and showing the orientation of terminus probes and internal fragment probes for use in conjunction with this adapter modified restriction fragment. The Xs represent bases of restriction fragment, excluding the restriction site bases. The Y's represent complemnentary bases on the other strand, excluding the restriction site basess. The variable region of the terminus probes is indicates by bases $Y_1$–$Y_5$. The terminus probe is indicated by bases $Y_6$–$Y_{10}$ In step A, an adapter is joined to a restriction fragment. In step B, a terminus probe is shown in alignment with the adapter-modified restriction fragment. In step C, a terminus probe and internal fragment probe are shown in alignment with the adapter-modified restriction fragment.

The "variable region" of a terminus probe may be located either 5' or 3' with respect to the constant region. The selection of the relative orientation of the variable region with respect to the constant region in a given embodiment of the invention will vary in accordance with choice of which strand of the adapter-modified restriction fragment is selected for analysis and in accordance with the choice of which terminus of the adapter-modified restriction fragment is to be analyzed (see FIG. 1).

(2) The term "a set of terminus probes" as used herein refers to a plurality of different terminus probes used in conjunction with each other, wherein each probe in the set has a functionally identical constant region, e.g., all of the constant regions are identical or have essentially the same sequence-specific hybridization properties, and the variable regions are different from one another. The term "A complete set of terminus probes" refers to a set of terminus probes that includes all possible nucleotide variable sequences (for the four major nucleotide bases, A, C, G, and T, or functional equivalents thereof). All variable regions of the oligonucleotides in a set of terminus probes are the same length. Thus the number of different terminus probes required to form a complete set of terminus probes increases with the length of the variable region. The number of different oligonucleotides required to form a complete set increases with the length of the variable regions in the terminus probes that form a set ($4^N$, wherein N is the length of the variable region).

(3) The term "internal fragment probe" refers to an oligonucleotide that may hybridize to a strand of an adapter-modified restriction fragment for analysis at a position immediately adjacent to the location on the strand to which a terminus probe may hybridize. Internal fragment probes hybridize to the nucleotide of the restriction fragment portion of adapter-modified restriction fragments, but do not hybridize to the adapter sequence.

(4) The term "complete set" as used in reference to internal fragment probes refers to a set of oligonucleotides having all possible nucleotide bases (of the four major nucleotide bases, A, C, G and T or equivalents thereof) for length of the oligonucleotide. All oligonucleotides in a complete set are of the same length. The number of different oligonucleotides required to form a complete set increases with the length of the oligonucleotides in a set ($4^N$, wherein N is the oligonucleotide length).

(5) The term "oligonucleotide array" as used herein refers to a solid support that has a plurality of different oligonucleotides attached at pre-determined spatial locations on the solid support. The support may be in any of a variety of shapes. In preferred embodiments of the invention, the solid support is substantially planar and the different oligonucleotides are arranged in a two-dimensional matrix. Oligonucleotide arrays may be prepared by a variety of methods well known to those skilled in the art. Such methods include the spotting of oligonucleotides on to the solid support, photolithographically controlled in situ synthesis on the solid support using phosphoramidites with photolabile protecting groups, and in situ synthesis on a solid support using conventional phosphoramidites. Various methods of synthesizing oligonucleotide arrays have described and can be found in, among other places, U.S. Pat. Nos. 5,510,270; 5,405,783; 5,143,854; 5,489,678; 5,733,509; 5,412,087; 5,436,327; and PCT Publication WO 95/25116. There is a pre-determined correlation between a given spatial location on the solid support of the array and the particular oligonucleotide located at that given spatial location that is created during the synthesis of the array. Thus, by referring to a particular spatial location on the array, the nucleotide base sequence of the oligonucleotide present at that spatial location may be known.

(6) The term "feature" as used herein with respect to oligonucleotide arrays and sorting arrays refers a group of essentially functionally identical macromolecules, e.g., oligonucleotides, at a pre-determined location on an array.

(7) The term "oligonucleotide" as used herein is used broadly to refer to any naturally occurring nucleic acid, or any synthetic analogs thereof, that have the chemical properties required for use in the subject methods, e.g., the ability to sequence specifically hybridize different polynucleotides. Thus, examples of oligonucleotides include DNA, RNA, phosphorthioates PNAs (peptide nucleic acids), phosphoramidates and the like. Method for synthesizing oligonucleotides are well known to those skilled in the art, examples of such synthesis can be found for example in U.S. Pat. Nos. 4,419,732; 4,458,066; 4,500,707; 4,668,777; 4,973,679; 5,278,302; 5,153,319; 5,786,461; 5,773,571; 5,539,082; 5,476,925; and 5,646,260.

(8) The terms "sorting array" and "sorting subarray" refer to an array formed by an array sorting signal receptors that are attached a fixed pre-determined spatial location on a solid support. There is a pre-determined correlation between a given spatial location on the solid support of the array and the sorting signal receptor located at a given spatial location that is created during the manufacture of the array. Thus, by referring to a particular spatial location on a sorting signal array, the identity of the sorting signal receptor at that particular spatial location may be known. An oligonucleotide array may be an embodiment of a sorting signal array. Preferred sorting arrays for use in the invention are oligonucleotide arrays.

(9) The term "array sorting signal" as used herein refers to a member of a specific binding pair. The second member of the specific binding pair is referred to as an array sorting signal receptor. In a preferred embodiment of the invention, the array sorting signals are oligonucleotides.

(10) The term "array sorting signal receptor" as used herein refers to a member of a specific binding pair. The second member of the specific binding pair is an array sorting signal. In a preferred embodiment of the invention, the array sorting signals are oligonucleotides.

(11) The term "specific binding pair" as used herein refers to a pair of molecules, typically macromolecules, that specifically bind to each other. Each member of the specific binding pair may be referred to as a "specific binding pair member." Examples of specific binding pairs include, complementary oligonucleotides, antibody-antigen pairs, lectin-sugar pairs, receptor-ligand pairs, and the like. Preferably, specific-binding pair members bind to each other with high affinity as well as high specificity.

(12) The term "representative restriction fragment" refers to a polynucleotide restriction endonuclease digestion product that is derived from a larger polynucleotide in such a way as to produce a predetermined constant number, preferably one, restriction fragment for the polynucleotide from which the representative restriction fragment was derived. For example, a representative restriction fragment of a 4.5 Kb cDNA may be a 0.8 Kb subfragment having EcoRI and Hind III generated termini and produced by treating the cDNA with the indicated restriction endonuclease. Although the representative restriction fragments are preferably formed through the use of restriction endonuclease digestions of polynucleotides, it will be appreciated by those skilled in the art that the functional equivalents of representative restriction fragments can be produced by the sequence specific cleavage mechanisms other than the use of restriction endonucleases, e.g., oligonucleotides joined to metallic cations. The term "representative restriction fragment," as used herein may refer collectively to representative restriction fragments, adapter-modified representative restriction fragments, and the amplification products of adapter-modified representative restriction fragments. Those instances in which the term "representative restriction fragment" refers only to representative restriction fragment, will be apparent by virtue of the context in which the term is used, e.g., the subsequent manipulations to be performed on the representative restriction fragment. Similarly, the term "restriction fragment" may be used herein to include "representative restriction fragments" as well as conventional restriction fragments. By virtue of context, it will be apparent to those skilled in the art when the term should be construed to exclude representative restriction fragments.

(13) The terms "restriction endonuclease recognition site" and "recognition site" as used herein refers not only to the nucleotides that form a restriction endonuclease recognition site, but also includes: (1) residual nucleotides that were part of a recognition site and remain after restriction endonuclease digestion, (2) nucleotides that are complementary to the residual nucleotides that were part of the recognition site and remain after restriction endonuclease digestion (and subsequent manipulations). By virtue of the context in which the term is used, it will be readily understood by a person skilled in the art that when term "restriction fragment endonuclease recognition site" refers to complete recognition site and when the term refers to the portion of the recognition site that remains after digestion and subsequent manipulations.

(14) The term "fingerprint" as used herein refers to a set of data relating to a complex polynucleotide population in which the relative concentrations of the different polynucleotide that formed the population are measured.

(15) The term "identifier sequence" as used herein refers to a small (e.g., 10–30 base pairs in length) polynucleotide sequence that is present in a larger polynucleotide. The identifier sequence is of sufficient length to permit the identification of a larger polynucleotide comprising the identifier sequence. The identifier sequence may be of contiguous or non-contiguous base sequence information. Preferably, the identifier is a contiguous sequence of nucleotide bases.

(16) The term "marker" as used herein, refers to a compound or method for tracking the identity of an oligonucleotides of known base sequence. A marker may be specifically associated with a given oligonucleotide, the base sequence of the nucleotide may be determined because of the predetermined correlation between the base sequence of the oligonucleotide and the marker. The specific oligonucleotide associated with a marker is said to be "marked."

(17) The term "adapter" as used herein refers to a double-stranded oligonucleotide having a terminus that is capable of being joined to the terminus of a restriction fragment. The terminus of the adapter may have a 3' overhand, a 5' overhang, or may be blunt-ended. As the terminus of the adapter is designed to be complementary to the terminus of a restriction fragment produced by a given restriction endonuclease, the nature of the terminus of the adapter will vary in accordance with the nature of the termini of the restriction fragments for ligation. The terminus nucleotide moieties of the adapter are selected so as to be compatible with the particular joining method used to join the adapter to the restriction fragment of interest. For example, when the joining is catalyzed by a DNA ligase, the 5' terminal nucleotide is phosphorylated and the 3' terminal nucleotide has a hydroxy group. Adapters for use in the subject methods comprise sufficient additional nucleotide (additional with respect to those nucleotides that are required to form an overhanging terminus) to permit the adapter to be used as a site for primer binding in a nucleic acid amplification reaction, e.g., PCR. In preferred embodiments of the invention, the nucleotide bases of the adapter terminus for joining a restriction fragment are selected so as to not recreate the restriction endonuclease site used to generate the terminus of the restriction fragment. Guidance on the joining of adapters to restriction fragments can be found in, among other places, U.S. Pat. Nos. 5,093,245 and 5,366,877.

(18) The term "joining" as used herein, with respect to oligonucleotides or polynucleotides refers to the covalent attachment of two separate nucleic acids to produce a single larger nucleic acid with a contiguous backbone. Preferred methods of polynucleotide joining are ligase (e.g., T-4 ligase) catalyzed reactions. However, non-enzymatic ligation methods may also be employed. Examples of ligation reactions that are non-enzymatic include the non-enzymatic ligation techniques described in U.S. Pat. Nos. 5,780,613; 5,476,930, which are herein incorporated by reference.

DESCRIPTIONS OF SPECIFIC EMBODIMENTS

The present invention relate to methods and compositions for simultaneously analyzing multiple different polynucleotides of a polynucleotide composition comprising multiple diverse polynucleotide sequences. The subject methods and compositions may also be applied to analyze or identify single polynucleotides; however, the subject methods and compositions are particularly useful for analyzing large diverse populations of polynucleotides, e.g., cDNA libraries. Most embodiments of the invention involve hybridizing terminus probes (of known base sequence) and internal fragment probes (of known base sequence) at adjacent positions on an adapter-modified restriction fragment generated from polynucleotide for analysis, and subsequently joining the terminus probes and internal fragment probes to each other. The terminus probe hybridizes to bases of a restriction endonuclease recognition site present at the terminus of a restriction fragment generated from the polynucleotide for analysis. Internal fragment probes hybridize to the same strand of the restriction fragment that the terminus probe hybridizes to and hybridizes to the restriction fragment portion of adapter-modified representative restriction fragments. The terminus probes and internal fragment probes may be marked so as to facilitate the simultaneous testing of multiple polynucleotides for the presence of many possible nucleotide base sequences.

Analysis of polynucleotide populations in accordance with methods of the invention may be used to provide one or more of the following types of information: (1) the nucleotide sequence of one or more polynucleotides in a complex polynucleotide composition, (2) partial nucleotide sequences of one or more polynucleotides in a complex polynucleotide composition, or (3) the relative concentrations of one or more different polynucleotides in a complex polynucleotide composition. Analysis of large complex populations of polynucleotides by the subject methods may be used to produce sufficient information about a polynucleotide population that differences between polynucleotide populations may be ascertained. Thus in some embodiments of the invention, "fingerprints" of a given polynucleotide population may be compared with "fingerprints" of other complex polynucleotide populations so as to determine differences in gene expression between the two populations. In addition to providing fingerprints of complex polynucleotide populations, some nucleotide base sequence information may be obtained for one or more polynucleotides in the population. An important example of a polynucleotide composition that may be analyzed by the invention is a cDNA preparation derived from an RNA population. The analysis of polynucleotide mixtures, particularly cDNA preparations, has numerous practical uses such as measuring gene expression for diagnostic or research purposes. Of particular interest are embodiments of the present invention that permit the majority of different polynucleotides in an RNA population may be detected.

The identity or expression of a particular polynucleotide of interest may be ascertained (or at least partially determined) by producing a short identifier sequence derived by combining from the nucleotide base sequence information obtained from (1) the hybridization of a terminus probe and an internal fragment probe, each of known base sequence, at adjacent positions on a polynucleotide of interest, and (2) the recognition site of a restriction endonuclease used to generate the polynucleotide molecule of interest. The combining of the different base sequence information inputs to produce an identifier sequence may be carried out by a programmable calculating device, e.g., an electronic computer, so as to conveniently automate the process when applied to complex polynucleotide populations. An identifier sequence may consist of contiguous or non-contiguous base sequence information. In a typical embodiment, (1) a terminus probe hybridizes to a strand of an adapter-modified representative restriction fragment at a position that includes the junction between the restriction fragment and the adapter, (2) an internal fragment probe hybridizes to the restriction fragment at a position immediately adjacent to a terminus of the hybridized terminus probe, and (3) the terminus probe and the internal fragment probe are subsequently joined together, e.g., by ligation. An identifier sequence may be used to produce oligonucleotide primers or probes to isolate the polynucleotides from which the identifier sequence was derived. Multiple identifier sequences may be obtained in parallel, thereby permitting the rapid characterization of a large number of diverse polynucleotides. Parallel processing may be achieved by differentially marking terminus probes or internal fragment probes. Parallel processing may be achieved by using ordered arrays of oligonucleotides that are terminus probes.

Preferred embodiments of the invention employ sets of first and second oligonucleotides of known sequence that are used in combination to hybridize to restriction fragments for analysis. These first and second oligonucleotides are the terminus probes and internal probes used in the subject methods. By using two sets of oligonucleotide probes in combination with each other, the total number of different oligonucleotides used to analyze most of the different polynucleotides in a complex nucleotide population is sharply reduced. For example, by using a first set of all possible 5-mers ($1024=4^5$) and a second set of all possible 5-mers (1024), in combination with each other, 1,048,576 ($4^{10}=4^5 \times 4^5$) different 10 base combinations may be interrogated with only 2048 different probes. As there are approximately 100,000 genes expressible in a human cell, two sets of 5-mer oligonucleotides may be used to conveniently divide a cDNA population derived from a human cell (or comparably complex eukaryotic cell) into several separate groups containing sufficiently small numbers of different restriction fragments so as to provide for the convenient analysis of the cDNA libraries and other complex polynucleotide compositions. Additional sequence information about the polynucleotides for analysis may be obtained from restriction endonuclease recognition sites in the polynucleotides for analysis. For example, the restriction endonuclease EcoRI has a 6 base pair recognition sequence. Thus, for example, by combining the sequence information obtained from identifying which two 5-mer oligonucleotides hybridize adjacent to an EcoRI recognition site, 16 bases of sequence information may be obtained so as to provide a unique identifying sequence that may be used to search sequence databases, prepare hybridization probes, or prepare amplification primers.

Pools of internal fragment probes, each of known sequence and labeled with a distinctive detectable label, may be used to decrease the number of steps necessary to obtain an identifier sequence for a given representative restriction fragment in the subject methods. For example, four different internal fragment probes may be simultaneously tested for the ability to hybridize adjacent to the terminus of a terminus probe hybridized to a representative restriction fragment, if each of the four different oligonucleotides is labeled with a different detectable label, i.e. a fluorescent dye, the presence of a particular label being indicative of the hybridization of the oligonucleotide modified by the label. If four different labels were not used, the alternative would have been to employ four separate hybridization reactions. Thus, the degree of savings in manipulation steps is in part directly proportional to the number of different differentially labeled oligonucleotide probes used in the hybridization steps.

In a preferred embodiment of the invention, the restriction fragments for analysis are representative restriction fragments. The use of representative restriction fragments rather than more complex mixtures of restriction fragments minimizes quantitation problems associated with attempting to correlate the analysis of multiple restriction fragments derived from each polynucleotide for analysis. By measuring the quantity of a representative restriction fragment produced from a polynucleotide composition, the quantity of the larger polynucleotide from which the representative restriction fragment was derived may be conveniently measured. Similarly, the relative quantities of different polynucleotides may be compared by comparing the relative quantities of different representative restriction fragments.

Embodiments of the invention include many different methods of analyzing polynucleotides. One embodiment of the subject methods includes the steps of: (1) forming a restriction fragment (preferably a representative restriction fragment) from a polynucleotide for analysis, (2) hybridizing a terminus probe to a single strand of the restriction fragment at a position on the restriction fragment that includes the restriction endonuclease-generated terminus, (3) hybridizing an internal fragment probe to the same strand of the restriction fragment such that the terminus probe is hybridized at a position immediately adjacent to the terminus probe, and (4) joining the terminus probe to the internal fragment probe. Terminus probes and internal fragment probes may be marked so as to facilitate the parallel analysis of multiple constituents of a complex polynucleotide population. Terminus probes are preferably marked by their spatial location on an oligonucleotide array and internal fragment probes are preferably marked by a fluorescent dye. The markers on the terminus probes and internal fragment probes that have been joined together may then be ascertained in accordance with the specific marking techniques used.

In a preferred embodiment of the invention, at least one adapter is joined to a restriction endonuclease-generated terminus of a representative restriction fragment, more preferably, two adapters are ligated to the two termini of the representative restriction fragments. The adapters are joined to the restriction fragment termini prior to hybridization of the restriction fragments to terminus probes and internal fragment probes. The amplification of the fragment by PCR (or a similar nucleic acid amplification technique) through the use of primers that can anneal to strands of the adapters. Additionally, the adapters may be used to recover of the restriction fragment from which an identifier sequence is derived, e.g., by performing PCR with a primer derived from the identifier sequence and a second primer specific for an adapter joined to the terminus that did not hybridize to the relevant terminus probe. Furthermore, an adapter may be used as a template for facilitating the hybridization of the terminus probe to the restriction fragments for analysis.

Junctions are formed at the site of joining between the termini of the representative restriction fragment and the adapters. Terminus probes are designed to hybridize to the nucleotides forming one of these junctions, i.e., to hybridize to regions of the restriction fragment and adapter that are adjacent to the junctions. Because the adapters are the same or contain regions with a common or substantially similar polynucleotide sequence, the terminus probes that are used to hybridize to the adapter modified representative restriction fragments have a constant region for hybridizing to the adapter and to terminal restriction endonuclease recognition site. Additionally, the terminus probes have a variable region for hybridizing to the restriction fragment nucleotides adjacent to the restriction endonuclease recognition site at the terminus. The variable regions of the terminus probes serve to divide the adapter-modified restriction fragments into subgroups based on their base sequences adjacent to a terminal restriction endonuclease recognition site.

In a preferred embodiment of the invention, adapter modified representative restriction fragments are amplified in a nucleic acid amplification reaction, e.g., PCR. The product of the amplification product are referred to herein as "adapter-modified representative restriction fragment amplification fragments." The terms "adapter-modified representative restriction fragment amplification products" and "adapter-modified representative restriction fragments" may be used interchangeably in the methods described herein unless indicated otherwise by the context of usage of the term. A nucleic acid amplification step may be used when the signal from the adapter-modified restriction fragments is not sufficient for the production of useful levels of detectable signal in the given polynucleotide sample for analysis.

Terminus probes and internal fragment probes as used in the subject methods are identified with a "marker" that is correlated with to the base sequence of the oligonucleotide. Thus by identifying the marker specifically associated with a given oligonucleotide, the base sequence of the nucleotide may be determined because of the predetermined correlation between the base sequence of the oligonucleotide and the marker. The marker may take on any of a variety of different forms. Such marker forms include: predetermined locations on arrays, fluorescent tag molecules, chromophore tag molecules, chemiluminescent tag molecules, specific binding pair members, temporally distinct addition of oligonucleotides, and the spatially distinct addition of oligonucleotides. Different forms of markers may be used alone or in combination with one another.

In one embodiment of the invention, the terminus probes marked by virtue of predetermined locations on a solid support, e.g., an oligonucleotide array. Thus by knowing the base sequence of a polynucleotide feature at a particular spatial location of an array, the complementary base sequence of a strand of the adapter modified restriction fragment that hybridizes to the array at the specific location may be ascertained. Thus, the array serves to "spatially" mark terminus probes.

In those embodiments of the invention in which the terminus probe is a feature of an oligonucleotide array, the internal fragment probe may be marked so as to distinguish themselves from one another by virtue of the spatial location on the array to which the internal fragment probe is added. The use of oligonucleotide arrays in various embodiments of the invention may serve one or more functions. First by employing arrays of different oligonucleotides, a given restriction fragment may be simultaneously tested for the ability to hybridize to a large number of different terminus probes of a known sequence. Second, multiple restriction fragments may be tested for the ability to hybridize to a terminus probe on the array.

In preferred embodiments of the invention, spatial marking may be achieved by providing an oligonucleotide array divided into various subarrays, wherein each subarray comprises essentially the same set of oligonucleotides features (in the same or different spatial arrangement from each other). For example, an array of terminus probes having variable regions 5 nucleotides in length may comprise 1024 identical subarrays, wherein, each of the subarrays is identical to each other and is formed by 1024 different terminus probes. The subarrays may be organized in such a way as to permit an oligonucleotide solution to be added to one subarray without contacting the other subarrays. In this example, 1024 internal fragment probes (all possible 5-mer sequences) are separately added to each of the different subarrays. The identity of the internal fragment probe may thus be tracked by virtue of the specific subarray to which it is added. The spatial marking effect of using multiple subarrays may be achieved using an equivalent system multiple distinct arrays on separate solid supports.

In other embodiments of the invention, the internal fragment probes may be marked by virtue of temporal properties assigned to oligonucleotides of known sequence. The term "temporal properties" or "temporal marking" refer to methods employing the sequential addition of oligonucleotides. For example, (1) adapter-modified representative restriction fragment amplification products may be hybridized to terminus probes that are features of an oligonucleotide array, (2) then the hybridized adapter-modified restriction fragments are contacted with a internal fragment probe, (3) the internal fragment probe is then hybridized to the terminus probe, (4) the array is then analyzed, i.e., interrogated, so as to determine which features have been joined to internal fragment probes steps (2)–(4) are then repeated several times with a different internal fragment probe. Thus, by using successive rounds of hybridization with different internal fragment probes and correlating the hybridization round with the probes used during that particular round of hybridization, the internal fragment probes may be distinguished from one another. The different internal fragment probes used in temporal marking may be the same or different from one another.

Another method of using a "marker" to identify an oligonucleotide probe is by means of different detectable labels, e.g., fluorescent dye molecules. Detectable labels are chemical compounds that may be detected in relatively small amounts by virtue of their chemical or physical properties. Detectable labels may take on any of a variety of forms such as fluorescent dyes, chromophores, chemiluminescent molecules, radioactive isotopes, spin labels, enzymes, and the like. A wide variety of labels and labeling techniques may be used to mark probes, with the identifying criteria that the label/labeling method should not significantly interfere with. The detectable labels may be detected either directly or indirectly. Indirect detection employs a chemical intermediate that produces the signal detected by the actual detection device employed. Examples of indirect labeling include enzymes used with a fluorescent substrate, biotin labels used in conjunction with enzymatically labeled avidin, used in conjunction with fluorescently labeled antibodies, and the like. Chemical tags such as fluorescent dyes and other detectable labels permit multiple oligonucleotides (e.g., internal fragment probes to be used together in the same solution. Detectable labels are also of interest because, depending upon the particular detection scheme employed, they permit the quantitative (or semi-quantitative) detection of the label and hence the quantitative (or semi-quantitative) detection of the probe joined to the detectable label. In a preferred embodiment of the invention, the detectable labels employed are fluorescent dyes. An example of how to use probes marked with detectable labels is as follows. For example, (1) adapter modified representative restriction fragment amplification products may be hybridized to terminus probes that are features in an array, (2) then the hybridization adapter-modified restriction fragments are contacted with a pool of four different internal fragment probes, wherein each of the internal fragment probes are labeled with a distinct fluorescent dye that is correlated with the base sequence of the internal fragment probes, (3) the internal fragment probes are joined to the terminus probes that have hybridized to the adapter-modified restriction fragment amplification products, (4) the array is then interrogated so as to identify the specific fluorescent labels that have been attached to specific oligonucleotide features. Methods and compounds for attaching detectable labels to oligonucleotides are well known to those skilled in the art. Examples of such methods can be found in Hermanson, *Bioconjugate Techniques*, Academic Press, San Diego (1996); U.S. Pat. Nos. 5,366,860;

5,231,141; 5,188,937; 4,605,735; 4,667,025; 4,789,737; and 4,820,812. The specific methods and instrumentation suitable for detecting a specific detectable label will vary in accordance with the physical and chemical properties of the label. Such methods and instrumentation are well known by those skilled in the art. Examples of such methods and instrumentation can be found in U.S. Pat. No. 5,324,633 and PCT Patent Application No. WO 95/22068.

A detailed example of using detectable chemical labels and spatial marking is as follows. A cDNA library is prepared. Representative restriction fragments are formed from the cDNA library, The representative restriction fragments have a Hind III derived terminus and a EcoRI derived terminus. Adapters specific for the Hind III terminus and the EcoRI terminus are ligated to the representative restriction fragments, thereby forming adapter-modified representative restriction fragments. The adapter-modified representative restriction fragments are mixed with a pair of amplification primers specific for the adapters used to generate the adapter-modified representative restriction fragments and subjected to a PCR amplification reaction so as to generate a set of adapter-modified representative restriction fragment amplification products. The amplification products are then added to an array of terminus probes. The array comprise 256 identical subarrays, each subarray comprising a complete set of 1024 terminus probes. Each of the terminus probes has a constant region designed to be complementary to a strand of the adapter joined to the Hind III terminus of the representative restriction fragments. The terminus probes have a 5 nucleotide variable region on their 3' end. To each subarray is added a different solution comprising four different internal fragment probes, each probe being labeled with different fluorescent dye capable of being distinguished from one another based on their spectroscopic properties. Each internal fragment probe is 5 nucleotides in length. Thus, a complete set of 5 nucleotide internal fragment probes is prepared and distributed among 256 separate solutions. The internal fragment probe containing solutions are added to each subarray in such a manner that the solution added to a given subarray does not contact other subarrays. A DNA ligase is added in order to catalyze the joining of internal fragment probes that have hybridized at adjacent positions on an adapter-modified representative restriction fragment. The array is subsequently washed to remove terminus probes that have not been joined to the array as well as removing the adapter-modified representative restriction fragments. The array is the scanned in fluorescence detection imaging device capable of (1) spectrally resolving the four fluorescent dyes originally attached to the internal fragment probes and (2) determining the location of the dye on the array. The base sequence of the terminus probes that have been joined terminus probes and the base sequence of the terminus probes may then be combined with each other and the Hind III recognition sequence to produce identifier sequences corresponding to the different cDNAs in the original library. Moreover, the intensity of the fluorescence is indicative of the relative concentrations of the cDNAs in the library.

In another embodiment of the invention, specific binding pair members may be used to mark the terminus or internal fragment probes of known sequence. Of particular interest are the use of specific binding pair members, the pair of members being (i) array-sorting signals and (ii) array-sorting signal receptors. In preferred embodiments of the invention, the array sorting signals are single-stranded oligonucleotides and the array-sorting signal receptor are complementary oligonucleotides. By attaching array-sorting signals to the terminus probes or internal fragment probe, the methods of the invention may be used in such way that the joining of the terminus probe and internal fragment probes takes place in solution rather than on a solid phase (e.g., an array). In those embodiments of the invention employing array-sorting signals on the terminus probes or internal fragment probes marked with array-sorting signals, a sorting array, i.e., an array of array-sorting signal receptors, is employed to be used in conjunction with the array sorting signals. By attaching an array-sorting signal receptor at a specific location on an array, the presence of an oligonucleotide having the cognate array-sorting signal may be detected. Array-sorting signals may be present on the terminus probes or internal fragment probes. In those embodiments of the invention in which terminus probes are marked with an array sorting signal, the internal fragment probes to be used in conjunction with such probes are preferably marked with a detectable label, e.g., a fluorescent dye. Conversely, in those embodiments in which internal fragment probes are labeled with an array sorting signal, the terminus probes to be used in conjunction with such probes are preferably marked with a detectable label, e.g., a fluorescent dye. The array sorting signals are preferably selected so as to minimize cross-hybridization between the different sorting signal and sorting signal receptors. In those embodiments of the invention employing oligonucleotides as sorting signals and sorting signal receptors, cross-hybridization may be avoided (or minimized) by selecting oligonucleotide sequences with minimal amounts of sequence homology between the different oligonucleotides.

In one embodiment of the invention employing array-sorting signals, (1) terminus probes are prepared, wherein each of the different terminus probes is labeled with a different array-sorting signal, (2) the terminus probes are hybridized to adapter-modified representative restriction fragments (or adapter-modified representative restriction fragment amplification products) prepared from the polynucleotide population of interest, (3) detectably labeled (e.g., fluorescently labeled) internal fragment probes are contacted with the terminus probes hybridized to the adapter-modified representative restriction fragments, (4) internal fragment probes that have hybridized adjacent to the terminus probes are joined to the terminus probes, (5) the polynucleotide products of the joined terminus probe and internal fragment probes pairs are then contacted with a sorting array, i.e., an array of array-sorting signal receptors, and (6) the array is then interrogated so as to detect those array-sorting signal receptors that have bound the detectable label of the internal fragment probes. Internal fragment probes alone cannot bind to the array because the internal fragment probes do not have array-sorting signals. Terminus probes that have bound alone to the array cannot be detected because the oligonucleotides lack detectable labels (e.g., fluorescent dyes). Thus, only the product of terminus probes joined to internal fragment probes are detected by arrays of receptor-sorting signals. In order to test large numbers of different terminus and internal fragment probes in parallel, the adapter-modified representative restriction fragments may be divided into several aliquots, to each aliquot may be added a complete set of terminus probes (each probe labeled with distinctive array sorting signals) and a subset of internal fragment probes. Each of the internal fragment probes in the subset may be labeled with a distinctive fluorescent label. After joining terminus probes and internal fragment probes to each other, each aliquot may be contacted with a separate subarray of array-sorting signal receptors. An example of an embodiment of the invention employing array sorting signals is as follows: (1) a mixture of adapter-modified representative restriction fragments may be divided into 256 separate aliquots, (2) to each aliquot is added a set of 1024 terminus probes, each oligonucleotide having a 6 base constant region and a five base variable region, wherein all possible variable regions are represented and each oligonucleotide is marked with a distinctive array-sorting signal, (3) to each aliquot is added a set of four different internal fragment probe 5-mers, each of the four different oligonucleotides labeled with a different fluorescent label; a total of 1024 different 5-mers covering all possible 5-base sequence variations is distributed among the 256 different aliquots, (4) after hybridization and the joining of the terminus and internal fragment probes is completed, each aliquot is distributed onto a separate array of array-sorting signals receptors, wherein each array or subarray has 1024 signal-sorting receptor specific for the array sorting signal on the terminus probes.

Formation of Representative Restriction Fragments

Many different methods of producing representative restriction fragments may be used to practice the methods of the invention. These methods of producing representative restriction fragments may be used interchangeably with the different embodiments of the invention. In embodiments of the invention that include the step of amplifying adapter-modified representative restriction fragments, it is preferred that the method of generating representative restriction fragments be a method that generates representative restriction fragments that are substantially the same length. Methods for generating representative restriction fragments of substantially the same length may employ type IIS restriction endonucleases as described below in this section.

Methods of preparing representative restriction fragments include the technique of sequential restriction endonuclease digestion with two restriction endonuclease (having different recognition sites) as applied to immobilized DNA fragments. For the sake of convenience, this technique may be referred to as "sequential restriction digestion." Examples of sequential restriction digestion include the following method and variations thereof. cDNA is prepared from an RNA preparation of interest. The cDNA is immobilized on a solid phase. A large representative sample of the cDNA components of the cDNA preparation are immobilized at the same end of the cDNA molecule (typically the end of the cDNA corresponding to the mRNA polyA tail is immobilized). The immobilized cDNA is then digested with a first restriction endonuclease. The released, i.e., not bound, restriction fragments may then be washed away. Thus, the restriction endonuclease digestion process results in the production of an immobilized cDNA fragment having a terminus generated by a restriction endonuclease. A first adapter may optionally be ligated to the cDNA termini produced by the first restriction enzyme at this time. The immobilized cDNA is then digested with a second restriction enzyme having a different recognition site than the first restriction endonuclease. A second adapter is then ligated to the cDNA termini produced by the second restriction endonuclease. The released cDNA restriction fragments, each having termini produced by different restriction enzymes, are then collected and may subsequently be joined to adapters specific for each of the two termini. If an adapter had not been previously ligated to the termini produced by the first restriction endonuclease digestion, then first adapters are ligated to these termini. After the second adapter has been ligated, formation of adapter-modified representative restriction fragments has been completed.

The cDNA fragments may be immobilized to a solid phase at a predetermined end of the cDNA by a variety of methods, provided such methods do not substantially interfere with subsequent restriction endonuclease or ligation reactions. In a preferred embodiment of the invention, cDNA is synthesized using a biotinylated polyT primer to initiate first strand synthesis (priming from the RNA polyA tail). The biotinylated portion of the cDNA is then complexed with immobilized streptavidin or avidin. Of course, many specific binding pairs, e.g., antibody-hapten pairs, may be substituted for avidin-biotin to achieve the same immobilization effect. The solid support may be of any of a variety of forms such as beads, sheets, membranes, chips, fiber, and the like. Similarly, the solid support may be formed of any of a number of materials compatible with immobilization of nucleic acids, including, but not limited to, glass or polymers, e.g., polystyrene, polyacrylamide, polycarbonate, polyethylene, polypropylene, agarose, and the like.

Most restriction endonucleases are suitable for use in the restriction endonuclease digestion steps of the subject method. Restriction endonucleases are widely available commercially, and procedures for using them are well known to persons of ordinary skill in the art of molecular biology. Suitable restriction endonucleases may produce either blunt ends or overhanging ends.

Type IIs restriction endonucleases may also be used as a restriction endonuclease in sequential restriction endonuclease digestion. Type IIs restriction endonuclease have recognition sites that are different than the cleavage site. Because Type IIs restriction endonucleases are of particular interest because they may be used to produce small representative restriction fragments of a uniform size because the property of type IIs enzymes to cleave at a fixed distance from the recognition site, irrespective of the cleavage sequence. To use a type IIs restriction endonuclease for sequential restriction endonuclease digestion, a first adapter having type II restriction endonuclease recognition site may be employed. For example, after digestion of immobilized cDNA fragments with a first restriction endonuclease, an adapter having a type IIs restriction endonuclease recognition site is ligated to the immobilized restriction fragments, the type IIs enzyme is then added, the dually digested restriction fragments are collected, and a second adapter is added (a polymerase catalyzed "filling-in" step may be used depending on the particular type IIs enzyme employed).

In order to maximize the degree of representation of an mRNA population among the representative restriction fragments. The initial cDNA preparation obtained from the cells of interest may be split into two portions and digested with the first and second restriction endonucleases in both possible temporal orders, i.e., representative restriction fragments are formed employing both possible orientations. For example, a cDNA population could be split into two fractions and immobilized at the 5' end on separate sets of streptavidin derivatized magnetic beads (sets A and B). Set A is first digested with Hind III, washed, and then digested with EcoRI. Set B is first digested with EcoRI, washed, and then digested with Hind III. Thus, the representative fragments from set A contains fragments from RNA transcripts that have an EcoRI site closer to the 5' end than the Hind II site. Similarly, the representative fragments from set B contains fragments from RNA transcripts that have a Hind III site closer to the 5' end than the EcoRI site. Thus, by splitting the cDNA preparation into two portions and digesting with restriction enzymes in both temporal order, the degree of representation may be greatly increased. Subsequent analysis by the subject methods employing internal fragment probes and terminus probes may be performed separately on the dual preparations of representative restriction fragments.

Another method of deriving unique polynucleotide fragments from larger polynucleotides is described in Sherman in U.S. Pat. No. 5,712,126 (Weisman and Prashar), which is incorporated by reference herein. An example of the method of producing representative restriction fragments as described in U.S. Pat. No. 5,712,126, involves selectively amplifying the 3' portion of an mRNA by (a) priming first strand cDNA synthesis with a primer that hybridizes to a polyA tail and has a 5' non-hybridizing sequence region that can be used for priming amplification, (b) synthesizing the second strand, (c) cleaving the double-stranded cDNA with a restriction endonuclease, (d) ligating an adapter to the cleavage fragments, wherein the adapter consists of two partially hybridized nucleic acid strands, wherein portions of the two strands are non-complementary to each other and portions of the two strands are complementary to each other, (d) amplifying the ligated cleavage fragments using a first primer whose sequence comprises at least a portion of the 5' sequence of the oligonucleotide primer of step (a) and a second primer with a sequence that comprises at least a portion of the sequence of one strand of the adaptor in the non-complementary portion, thereby selectively amplifying a DNA fragment comprising sequence complementary to a 3' end of the mRNA.

Addition of Adapters

Adapters are joined to the termini of representative restriction fragments in most embodiments of the invention. The adapters may be joined to the termini in the same joining reaction or in two joining reactions (e.g., ligation) performed sequentially. Two adapters may be joined to a representative restriction, such that a single adapter is joined to each terminus. The two adapters are different from one another. However, the two adapters may be sufficiently similar to one another so as to permit annealing and amplification with a single primer oligonucleotide rather than a pair of two different primers. Methods for joining adapters to restriction fragments are well known to those of ordinary skill in the art. Guidance in using adapters can be found in, among other places, U.S. Pat. No. 5,693,245.

Nucleic Acid Amplification

Adapter-modified representative restriction fragments may be amplified by a variety of primer-dependent polynucleotide amplification techniques. A variety of primer-dependent polynucleotide amplification techniques may be used for amplification. Such techniques include strand displacement amplification, 3SR amplification, and the like. The polymerase chain reaction (PCR) is particularly preferred for amplifying the adapter-modified representative restriction fragments. The polymerase chain reaction is described in, among other places, Diffenbach and Dveksler, *PCR Primer* Cold Spring Harbor Press, Cold Spring Harbor, N.Y. (1995) and U.S. Pat. No. 4,683,202; 4,683,195; 4,800, 159; 4,965,188; and 5,333,675.

In embodiments of the invention employing polynucleotide amplification, the primers for use in the polynucleotide amplification primers are selected so a to work in conjunction with the adapters used in the given embodiment. One or more different primers may be used for a given adapter. The primers are selected so as to specifically anneal to portions of the adapters that have been joined to the representative restriction fragments.

Hybridization of Terminus Probes to Representative Restriction Fragments

A terminus probe of a known sequence may be hybridized to a representative restriction fragment (including adapter-modified representative restriction fragments and amplification products thereof) using conventional nucleotide acid hybridization techniques. Examples of nucleic acid hybridization techniques can be found, among other places in Sambrook et al., *Molecular Cloning* Cold Spring Harbor Press, Cold Spring Harbor, N.Y. (1989). Nucleic acid hybridization parameters, e.g., time, temperature, salt concentrations, etc., may be varied to optimize the desired result.

Arrays

Other embodiments of the invention include oligonucleotide arrays having a set of oligonucleotide features, wherein the oligonucleotides of each feature have a constant region and variable region. The variable region is joined directly to the constant region at the 3' end of the constant region. The set of oligonucleotide features on an array of the invention includes all possible variations (i.e., a complete set of variations) of the nucleotide sequence of the variable region. The constant region is functionally constant between the different features of the subject arrays. The term "functionally constant" as used herein refers the property of either (1) being identical, or (2) being identical with respect to the portion of the constant region that is designed to hybridize to a representative restriction fragment or an adapter-modified representative restriction fragment. In the second case, additional nucleotide may be present on the 5' end of the oligonucleotides that form a feature. Both the constant region and the variable may vary in length in accordance with the particular embodiment of the invention. The length of the variable region is preferably between 3 and 12 nucleotides in length, 3–6 being more preferred. In a most preferred embodiment of the invention, the variable region of the features is five bases in length. Because a complete set of features comprise all possible nucleotide base sequence variations of the variable region, the number of features that constitute a complete set will vary in accordance with the (the number of possible bases raised to the power of the length in a nucleotide). Thus, in embodiments of the invention employing a five base variable region, a set of array features comprises $4^5=1024$ features. The length of the constant region is sufficient to hybridize to the selected restriction endonuclease recognition site of representative restriction fragments and to either all or part of the strand of the adapter joined to the selected restriction endonuclease recognition site of the representative restriction fragments and to either all or part of the strand of the adapter joined to the selected restriction endonuclease recognition site of a representative restriction fragment. The nucleotide base sequence of the constant region may or may not be preferably complementary to the relevant portion of the adapter modified representative restriction fragments. The constant regions are of sufficient length and of the proper nucleotide base composition to permit them to hybridize to a selected end of the adapter-modified representative restriction fragments. Upon hybridization with an adapter-modified representative restriction fragment, the double-stranded region formed between the adapter-modified representative restriction fragment and the constant region of the feature terminates at the nucleotide of restriction recognition site of the hybridized representative restriction fragment.

The arrays of the invention may comprise one or more subarrays. The subarrays that constitute a large array may each comprise essentially the same set of oligonucleotide features. The spatial arrangement of the oligonucleotide features of the different subarrays that constitute the larger array may be the same or different than each other. The subarrays may be physically isolated from one another so as to permit the application of one labeled oligonucleotide probe solution at one array without carrying over to other subarrays.

Kits

The invention also includes kits for performing one or more of the different methods for analyzing polynucleotide population described herein. Kits generally contain two or more reagents necessary to perform the subject methods. The reagents may be supplied in pre-measured amount for individual assays so as to increase reproducibility.

In one embodiment, the subject kits comprise adapters and primers for use with adapters to amplify adapter-modified restriction fragments. Kits may further comprise arrays of terminus probes or sets of internal fragment probes for use in conjunction with the adapters. Other embodiments of the subject kits include arrays of terminus probes and sets of internal fragment probes for use in conjunction with the terminus probes of the array. Still other embodiments of the subject kits include kits that comprise (1) sorting-signal receptor arrays and (2) terminus probes or internal fragment probes, wherein the probes are appropriately marked with sorting signals for use in conjunction with the sorting signal receptor array. Probes of the subject kits may be marked with detectable signals suitable for use in the subject methods. The kits of the invention may also include one or more additional reagents required for various embodiments of the subject methods. Such additional reagents include, but are not limited to: restriction enzymes, DNA polymerases, buffers, nucleotides, and the like.

INCORPORATION BY REFERENCE

All publications, patent applications, and patents referenced in the specification are herein incorporated by reference to the same extent as if each individual publication or patent application was specifically and individually indicated to be incorporated by reference.

EQUIVALENTS

All publications, patent applications, and patents mentioned in this specification are indicative of the level of skill of those skilled in the art to which this invention pertains. Although only a few embodiments have been described in detail above, those having ordinary skill in the molecular biology art will clearly understand that many modifications are possible in the preferred embodiment without departing from the teachings thereof. All such modifications are intended to be encompassed within the following claims. The foregoing written specification is considered to be sufficient to enable skilled in the art to which this invention pertains to practice the invention. Indeed, various modifications of the above-described modes for carrying out the invention which are apparent to those skilled in the field of molecular biology or related fields are intended to be within the scope of the following claims.

What is claimed is:

1. A method of analyzing a polynucleotide, said method comprising:
   forming a representative restriction fragment corresponding to the polynucleotide, wherein the representative restriction fragment has a first and second terminus and at least one of the termini is generated by a restriction endonuclease, hybridizing a terminus probe to a single strand of the restriction fragment at a position on the restriction fragment including the terminus generated by the restriction endonuclease, hybridizing an internal fragment probe to the single strand of restriction fragment at a position adjacent to the terminus probe, and joining the terminus probe to the internal fragment probe.

2. The method according to claim 1, said method further comprising the step of,
   combining (i) the nucleotide sequence information from the terminus probe with (ii) the nucleotide sequence information from the internal fragment probe and (iii) the nucleotide sequence of the recognition site of the restriction endonuclease used to produce the terminus, so as to produce an identifier sequence.

3. The method according to claim 1 wherein the polynucleotide is a cDNA.

4. The method according to claim 2 further comprising the step of comparing the identifier sequence with a DNA sequence database.

5. The method of claim 2 further comprising the steps of preparing a oligonucleotide hybridization probe comprising a base sequence encoding the identifier sequence.

6. A method according to claim 1, wherein the terminus probe is a feature of an oligonucleotide array.

7. A method according to claim 1 further comprising:
   of joining first and second adapters to the first and second termini of the representative restriction fragment, respectively, whereby an adapter-modified representative restriction fragment is formed, wherein the joining of the adapters to the termini occurs before the hybridizing of the terminus probe and the internal probe.

8. A method according to claim 7, further comprising the step of amplifying the adapter-modified representative restriction fragment, whereby amplification products of the adapter-modified representative restriction fragments are formed.

9. A method according to claim 8, wherein the step of hybridizing the terminus probe comprises
   contacting the amplification products with an oligonucleotide array under nucleic acid hybridization conditions, wherein the array comprises features that are terminus probes, said terminus probes having constant and variable regions, whereby a strand of the amplification product is hybridized to a terminus probe.

10. A method according to claim 9, wherein the step of hybridizing the internal fragment probe comprises,
    contacting the amplification product strand hybridized to a terminus probe with a solution comprising an internal fragment probe, wherein the contact occurs under nucleic acid hybridization conditions.

11. The method according to claim 10, wherein the solution comprises a plurality of internal fragment probes.

12. The method of claim 11, wherein each of the internal fragment probes is labeled with a different fluorescent label.

13. A method according to claim 12, further comprising the step of of contacting the hybridized amplification products with a second solution comprising at least one internal fragment probe that has a different nucleotide sequence than an internal fragment probe in the first solution.

14. A method according to claim 13, wherein the second solution comprises a plurality of different terminus probes, wherein each terminus probe in the second solution is labeled with a distinctive label.

15. A method according to claim 11, wherein the array comprises at least one subarray of 1024 distinct features, the variable region of each feature is five nucleotides in length, and each of the variable regions of the subarray has a different nucleotide sequence from the other variable regions of the terminus probes in the same subarray.

16. A method according to claim 12, wherein the constant region of the feature are at least 4 nucleotides in length.

17. A method according to claim 12, wherein the constant regions of the features are identical to each other.

18. A method according to claim 12, wherein the array comprises a plurality of subarrays wherein at least two of the subarrays comprise the same set of features.

19. A method according to claim 18, wherein the oligonucleotide probe solution comprises a plurality of internal probes and each different probe is labeled with a distinct identification label.

20. A method according to claim 19, wherein the oligonucleotide probes are labeled with different fluorescent labels.

21. A method according to claim 19, further comprising the step of of contacting the hybridized amplification products with a second solution comprising at least one internal fragment probe that has a different nucleotide sequence than an internal fragment probe in the first solution.

22. A method according to claim 21, wherein the second solution comprises a plurality of different terminus probes, wherein each terminus probe in the second solution is labeled with a distinctive label.

23. A method according to claim 7, wherein the internal fragment probe or the terminus probe comprises an array sorting signal.

24. A method according to claim 23, comprising the step of contacting the adapter-modified representative restriction fragment with an array comprising a plurality sorting signal receptors at a predetermined locations on the array.

25. A method according to claim 1, wherein the representative restriction fragment is generated by a method comprising the steps,
   immobilizing the polynucleotide on a solid support,
   contacting the polynucleotide with a first restriction endonuclease, whereby an immobilized restriction fragment is produced, and
   purifying the immobilized restriction fragment.

26. The method of claim 25, further comprising the steps of
   contacting the immobilized restriction fragment with a second restriction endonuclease, whereby the representative restriction fragment is produced, and
   purifying the representative restriction fragment.

27. The method according to claim 2, further comprising:
   joining a linker to the terminus produced by the first restriction enzyme on the immobilized restriction fragment, whereby an adapter-modified immobilized restriction fragment was produced, and contacting the adapter-modified immobilized restriction fragment with a second restriction endonuclease, whereby the representative restriction fragment is produced.

28. The method of claim 27, wherein the adapter comprises a type IIS restriction site and the second restriction endonuclease is a type IIS restriction endonuclease recognizes the type IIS restriction site in the adapter and cleaves within the immobilized restriction fragment.

29. A polynucleotide population analysis kit, said kit comprising,
   an oligonucleotide array comprising a plurality of terminus probes, and a a plurality of internal probes.

30. The kit according to claim 29, wherein the internal probes are in a first solution.

31. The kit according to claim 29, said kit further comprising a second solution, wherein the second solution comprises a plurality of internal probes, each of the internal probes in the second solution is labeled with a distinctive label, and at least one of the internal probes in the second solution has a different nucleotide base sequence than the internal probes in the first solution.

32. The kit according to claim 29, wherein the array comprises a plurality of subarrays.

33. A polynucleotide population analysis kit, said kit comprising:
   a sorting array comprising,
      a plurality of sorting signal receptors,
      a plurality of terminus probes marked with a sorting signal, wherein the sorting signals are specific for the sorting signal receptors on the sorting array, and a
      a plurality of internal fragment probes label with a detectable labeled, wherein at least two of the internal fragment probes are labeled with different detectable labels.

34. A polynucleotide population analysis kit, said kit comprising:
   a sorting array comprising a plurality of sorting signal receptors,
   a plurality of internal fragment probes marked with a sorting signal, wherein the sorting signal are specific for the sorting signal receptors on the sorting array, and a a plurality of terminus probes labeled with a detectable label, wherein at least two of the internal fragment probes are labeled with different detectable labels.

35. A method according to claim 23, wherein the array sorting signal and the sorting signal receptors are polynucleotides.

* * * * *